US006924640B2

United States Patent
Fickert et al.

(10) Patent No.: US 6,924,640 B2
(45) Date of Patent: Aug. 2, 2005

(54) OIL AND GAS WELL TUBULAR INSPECTION SYSTEM USING HALL EFFECT SENSORS

(75) Inventors: Gary Fickert, Houston, TX (US); John Haynes, Houston, TX (US)

(73) Assignee: Precision Drilling Technology Services Group Inc., Calgary (CA)

( * ) Notice: Subject to any disclaimer, the term of this patent is extended or adjusted under 35 U.S.C. 154(b) by 92 days.

(21) Appl. No.: 10/307,094

(22) Filed: Nov. 27, 2002

(65) Prior Publication Data

US 2004/0100256 A1 May 27, 2004

(51) Int. Cl.[7] .................. G01N 27/82; G01R 33/12; G01R 33/07
(52) U.S. Cl. .................. 324/221; 324/220; 324/235; 324/238
(58) Field of Search .................. 324/220–221, 324/228, 235, 238, 240, 367, 374–375; 166/253.1, 250.05, 250.08

(56) References Cited

U.S. PATENT DOCUMENTS

| | | | | |
|---|---|---|---|---|
| 3,538,433 A | * | 11/1970 | Wood et al. ................. | 324/227 |
| 3,543,144 A | * | 11/1970 | Walters et al. .............. | 324/221 |
| 3,940,689 A | * | 2/1976 | Johnson, Jr. ................. | 324/221 |
| 4,710,711 A | * | 12/1987 | Walkow ....................... | 324/221 |
| 4,751,461 A | * | 6/1988 | McWhirter et al. ......... | 324/221 |
| 5,036,283 A | * | 7/1991 | Trouiller et al. ............. | 324/375 |
| 5,119,023 A | * | 6/1992 | Lloyd .......................... | 324/239 |
| 5,293,117 A | * | 3/1994 | Hwang ........................ | 324/220 |
| 5,670,878 A | * | 9/1997 | Katahara et al. ............ | 324/221 |
| 5,747,998 A | * | 5/1998 | Fowler et al. .............. | 324/263 |
| 6,100,684 A | * | 8/2000 | Ramaut ....................... | 324/220 |
| 6,316,937 B1 | * | 11/2001 | Edens ........................ | 324/220 |

FOREIGN PATENT DOCUMENTS

| | | | | |
|---|---|---|---|---|
| JP | 3-51755 | * | 3/1991 | |
| JP | 03274455 A | * | 12/1991 | .......... G01N/27/83 |
| RU | SU 0739442 | * | 6/1980 | .......... G01R/33/00 |

OTHER PUBLICATIONS http://www.batelle.org/pipetechnology/MFL/Links/Sensor-Type.htm, Last modified: Sunday Oct. 1, 2000.*

Gwan Soo Park and Eun Sik Park, "Improvement of the Sensor System in Magnetic Flux Leakage–Type Nondestructive Testing (NDT)," IEEE Transactions on Magnetics, vol. 38, No. 2 Mar. 2002, pp. 1277–1280.*

* cited by examiner

*Primary Examiner*—Jay Patidar
(74) *Attorney, Agent, or Firm*—Patrick H. McCollum (57) ABSTRACT

An inspection system for detecting flaws in oil and gas well borehole ferromagnetic tubulars. The inspection device operates inside the tubular by first saturating tubular wall with magnetic flux. Flaws in the wall causes flux leakage, and the magnitude of the flux leakage are measured with Hall effect sensors disposed within the inspection device. The magnitude of flux leakage is then related to the amount of ferromagnetic material loss resulting from the flaw. Eddy currents induced in the wall are also measured and combined with the Hall effect sensor measurements to define location and geometric shape of the flaw.

28 Claims, 6 Drawing Sheets

OIL AND GAS WELL TUBULAR INSPECTION SYSTEM USING HALL EFFECT SENSORS

This invention is related to the detection of flaws in ferromagnetic material lining boreholes, and more specifically to the detection of pits, holes, splits, corrosion and other types of flaws in ferromagnetic tubulars used in oil and gas well boreholes penetrating earth formations. It also relates to the detection of material outside the lining, such as anchors and clamps

BACKGROUND OF THE INVENTION

In the context of this disclosure, the term "well borehole" refers to a borehole drilled to penetrate earth formations that contain fluids of interest. Boreholes penetrating hydrocarbon bearing earth formations are typically lined with ferromagnetic tubulars such as steel casing. This type of tubular, commonly referred to as borehole "casing", is used to maintain the physical integrity of the borehole. The annulus formed between the outside diameter of the casing and the inside diameter of the borehole is then filled with cement thereby hydraulically isolating various earth formations penetrated by the borehole. A series of holes or "perforations" are placed in the casing and surrounding cement adjacent to formations containing hydrocarbons. Fluids within these hydrocarbon bearing formations are then in fluid communication with the borehole, and can be "produced" at the surface of the earth via the borehole. The casing and cement sheath combine to isolate fluids in non-hydrocarbon bearing formations from hydrocarbon production.

To increase efficiency of the producing operation, and to produce from multiple hydrocarbon bearing formations within a given borehole, assemblies comprising tubing, packers and valves are used within the primary borehole casing. This methodology is known in the art. Tubing, like casing, is also typically steel.

Borehole conditions in hydrocarbon (gas and oil) producing wells are typically harsh. Temperatures can reach 150 degrees Centigrade (° C.) and higher. Tubulars are exposed to a variety of mechanical forces. Hydrostatic pressure is high. Fluids produced by the well, which typically include at least a fraction of saline water as well as hydrocarbons, are often highly corrosive. Damage can also occur in tubulars in injection wells that are used to dispose unwanted fluids in "disposal" formations penetrated by a well borehole. A borehole in "reversible fluid communication" with a formation penetrated by the borehole can, therefore, include both producing and injection wells. The term "reversible fluid communication" will also include, for purposes of disclosure, wells which are neither producing fluids or injecting fluids, but which are commonly referred to as "plugged" wells. All of these harsh borehole environmental effects in all types of wells can, over time, result in damage to the ferromagnetic tubulars within the well borehole. Damage or "flaws" can be in the form of loss of metal, both from the inside surface and from the outside surface of the tubular. This type of metal loss can occur over rather extensive axial lengths of tubulars. As an example, pits partially penetrating the tubular wall can form on the inner surface or the outer surface of the tubular. The physical location of the flaw is significant in formulating remedial steps to either impede or to repair the flaw. Holes completely penetrating the borehole wall are not uncommon. Tubulars can split axially due to a combination of corrosion and pressure. Scratches and gouges can occur from operation of mechanical devices within tubulars. Any type of tubular flaw can jeopardize the operational functions of the tubulars. More specifically, damage to casing can jeopardize the mechanical integrity of the borehole and hydraulic seal between formations penetrated by the borehole. Damage to production tubing can jeopardize effective production operations in a variety of ways. An effective system for detection of flaws in wellbore tubulars is important from both an economic and from a safety viewpoint.

Well boreholes can also drilled specifically to penetrate water bearing formations. These "water" wells can produce potable water, produce non-potable water for injection or other production operations. Water wells are also typically cased with ferromagnetic tubulars that function essentially the same as previously discussed tubulars in oil and gas well boreholes. Disposal wells are drilled specifically for disposal of unwanted fluids produced by other wells. Disposal wells are also typically cased with ferromagnetic tubulars In the context of this disclosure, the term "flaw" will be used to include any type of physical perturbation in a tubular including pits, holes, burrs, areas of wall thinning, splits, scratches, gouges and the like. The term will also include perturbations caused by corrosion, mechanical damage, and imperfections in manufacture.

EMBODIMENTS

1. Apparatus

Figure 1:
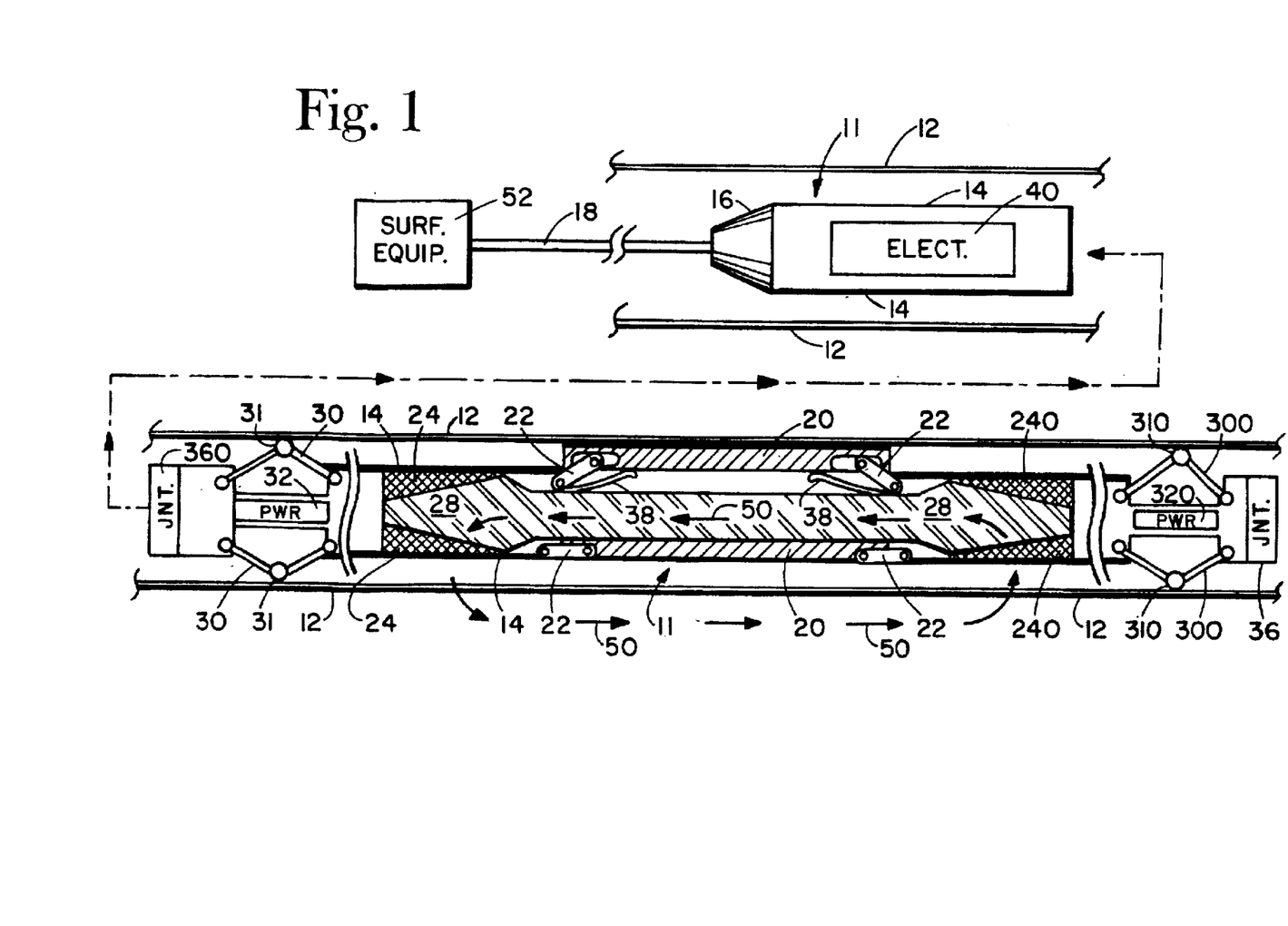
FIG. 1 is a sectional view of a tubular inspection tool illustrating basic physical components and structure.

An overview of the oil and gas well borehole tubular inspection system is obtained from a discussion of the sectional view of the tubular inspection system shown in FIG. 1. Alternately the system can be used in tubulars within water wells. The part of the system that exists in the borehole is denoted as a whole by the numeral 11, and will be referred to as the "tool". The tool 11 comprises a pressure housing 14, which is shown in position within a ferromagnetic tubular 12 that is to be inspected. The ferromagnetic tubular 12 is preferably magnetically saturated in the vicinity of the tool 11 by magnetic poles 24 and 240 at opposing ends of a core material 28. The magnetic field induced within the tubular 12 by the magnetic pole-core assembly is shown conceptually using the arrows 50. It should be understood that the field is induced with axial symmetry around the tool, although hypothetical arrows are shown only on one side of the drawing for clarity. The poles 24 and 240 are shown as permanent magnets. Alternately, electromagnets can be used. Electromagnets require a greater amount of electrical power to be supplied to the tool. Furthermore, more than two poles can be used.

The tool 11 is operated centralized within the tubular 12, as illustrated in FIG. 1. This is accomplished by preferably two power centralizers 30 and 300 disposed at opposing ends of the magnetic pole-core assembly. The centralizers 30 and 300 comprise rollers 31 and 310, respectively, which are urged against the inner wall of the tubular 12 by forces typically generated by springs 32 and 320, respectively. The rollers 31 and 310 reduce friction as the tool 11 is conveyed along the inner surface of the tubular 12. Preferably four centralizer roller assemblies are used at each axial position along the tool 11. The power sources 32 and 320 are preferably spring mechanisms. Alternately, the power sources can be electrical motors or hydraulic motors.

Again referring to FIG. 1, the tool 11 comprises a pad assembly containing a plurality of sensor pads 20. Only two pads 20 are shown for clarity, and are sufficient for purposes of illustration. Ten pads radially spaced around the tool 11 are preferred, although more or fewer pads can be used depending upon tubular size, desired measurement resolution, and other factors that will be discussed in subsequent sections of this disclosure. Each pad 20 is radially urged against the inner wall of the tubular 12 using pivot arms and springs 38. Alternately, the springs 38 can be replaced with electric or hydraulic motor devices thereby allowing the pads to be radially extended and retracted. The pad shown on the upper portion of FIG. 1 is shown extended against the inner wall of the tubular 12. The lower pad 20 is shown retracted so that it fits within the outer diameter of the tool 11. It should be understood that all pads are normally operated extended against the inner wall surface of the tubular, and that the lower pad is shown retracted only for purposes of illustration.

Still referring to FIG. 1, a joint 360 connects to a section of the tool 11 which contains an electronics section 40. Stated briefly, the electronics package is used to power and control various elements and obtain the sensor measurements within the downhole tool 11. Details of the electronics section will be presented in subsequent sections of this disclosure. The "up hole" end of the tool 11 is terminated by a cable head 16 which is operationally attached to a "down hole" end of a conveyance means 18 such as a logging cable. As mentioned previously, tools of other types (not shown) can be disposed between the tool 11 and the cable head 16. An opposing "up hole" end of the conveyance means 18 is operationally attached to surface equipment 52. The conveyance means can be a logging cable containing a single electrical or fiber optic conductor, a logging cable containing multiple electrical conductors, or a multiconductor logging cable comprising both electrical and fiber optic conductors. The conveyance means 18 can also comprise a coiled tubing string through which electrical communication is established. The "downhole" end of the tool 11 is terminated by a joint 36 to which additional types of sensing tools can be attached, or to which a "bull plug" can be attached in the absence of additional sensing tools (see FIG. 2).

As mentioned previously, the magnetic pole-core assembly magnetically saturates the tubular 12 in the vicinity of this assembly (see conceptual arrows 50). Any loss in the metal content or variation in the geometry of the tubular 12, which is defined as a tubular "flaw", creates a physical perturbation in the tubular. This perturbation results in flux leakage which, in turn, results in a change in the magnetic field at the point of perturbation. The magnitude of the change in magnetic field is a function of the amount and the geometry of the metal loss. The change in the magnitude of the magnetic field is sensed by preferably a plurality of Hall effect devices or Hall effect "sensors" disposed in each pad 20. The output voltage of a Hall effect sensor is proportional to the strength of the magnetic filed to which the sensor is exposed, within the constraints of the sensitivity range of the sensor. Any variation in magnetic field within the sensitivity range of a Hall effect sensor results, therefore, in a measurable change in sensor output voltage. This measured change in voltage can then be transformed into a determination of the amount of metal loss in the sensitivity range of the Hall effect sensor, and to a certain extent the geometry of the metal. Variations in AC voltage can be related to metal loss. Variations in DC voltage can be related to metal thickness.

Hall effect sensors alone can not be used to determine whether a detected flaw in on the inner surface or the outer surface of the tubular 12. Shallow reading sensors are used to detect flaws on the inner surface of the tubular 12. Reluctance measurements and eddy current measurements are the basis of two types of shallow reading sensors. A reluctance sensor may comprise a coil and a small magnet, and responds to changes in magnetic field resulting from a perturbing flaw on the inner surface of the tubular. An alternate reluctance sensor may comprise a Hall effect device. An eddy current sensor responds to any eddy currents created on the inner surface of the tubular by a perturbing flaw. Preferably two shallow reading sensors, with each comprising a coil, are disposed on each pad 20. These sensors are responsive to perturbing flaws on the inner surface of the tubular. If a Hall effect sensor detects a loss of metal and a response from a shallow response sensor is also measured, then it is concluded that the flaw is on the inner surface of the tubular 12. Conversely, if a Hall effect sensor detects a loss of metal and there is no measured response from a shallow response sensor, then it is concluded that the flaw is on the outer surface of the tubular 12.

Figure 2:
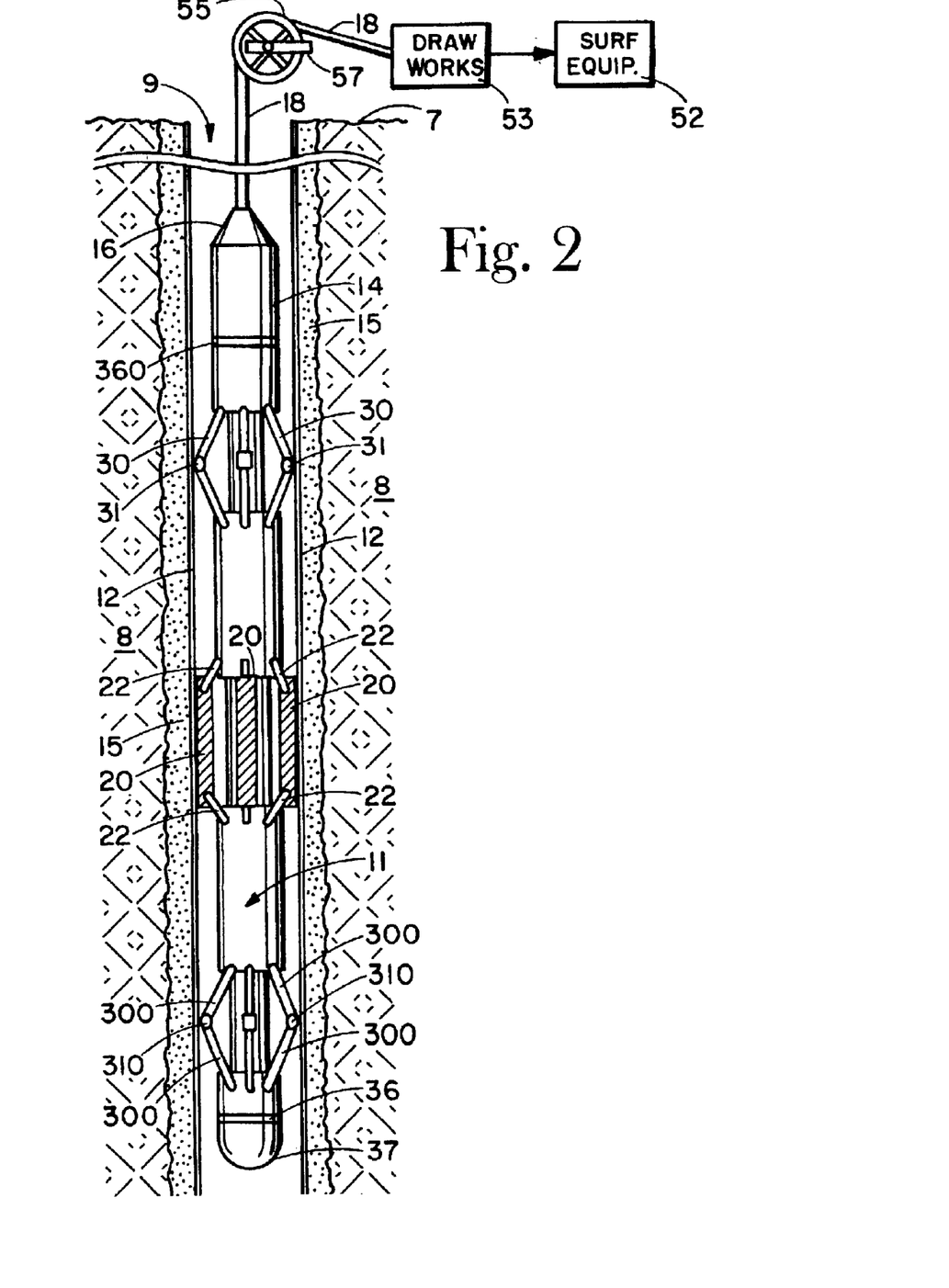
FIG. 2 illustrates the tubular inspection tool suspended centralized within a cased borehole.

FIG. 2 illustrates the tubular inspection tool 11 suspended within a borehole 9 by a conveyance means 18 which is preferably a logging cable attached to the cable head 16. It should be understood that other types of tools (not shown) can be operated "in combination" with the tubular inspection tool 11. These tools can be disposed between the tubular inspection tool 11 and the cable head 16. The borehole is cased with ferromagnetic (steel) tubular 12. A cement annulus 15 hydraulically isolates formation material 8 penetrated by the borehole 9. Centralizer arms 30 and 300 are extended urging rollers 31 and 310, respectively, against the inner wall of the tubular casing 12 thereby centralizing the tool 11 within the casing. Three of four centralizers arms, spaced radially at 90 degrees, are shown at each axial centralizing location. It should be understood, however, that as few as three centralizer arms, spaced radially at 120 degrees, or more than four centralizer arms, can be used at each axially centralizer location. Furthermore, centralizers can be disposed at more than two axial locations along the tool 11. Sensor pads 20 are shown extended by the arms 22 to contact the inner wall surface of the tubular 12. Only three pads are shown for purposes of clarity.

Still referring to FIG. 2, the down hole end of the tool 11 is terminated by a bull plug assembly 37 connected to the joint 36. Again, it should be understood that the tubular inspection tool 11 can be run in combination with other types of tools (not shown), and these tools can be disposed between the tool and the bull plug assembly 37. At the surface of the earth 7, the logging cable passes over a sheave wheel 55, which cooperates with a depth measuring device 57 to indicate the depth of the tool 11 within the borehole 9. The tool 11 is conveyed along the borehole 9 by draw works 53 at which the upper end of the logging cable 18 is terminated. The surface equipment 52 is in two-way communication with the tool 11 through the draw works 53 and via the cable 18. Power, telemetry, a surface processor and at least one data recording devices are preferably contained within the surface equipment 52, as will be discussed in subsequent sections of this disclosure.

Figure 3:
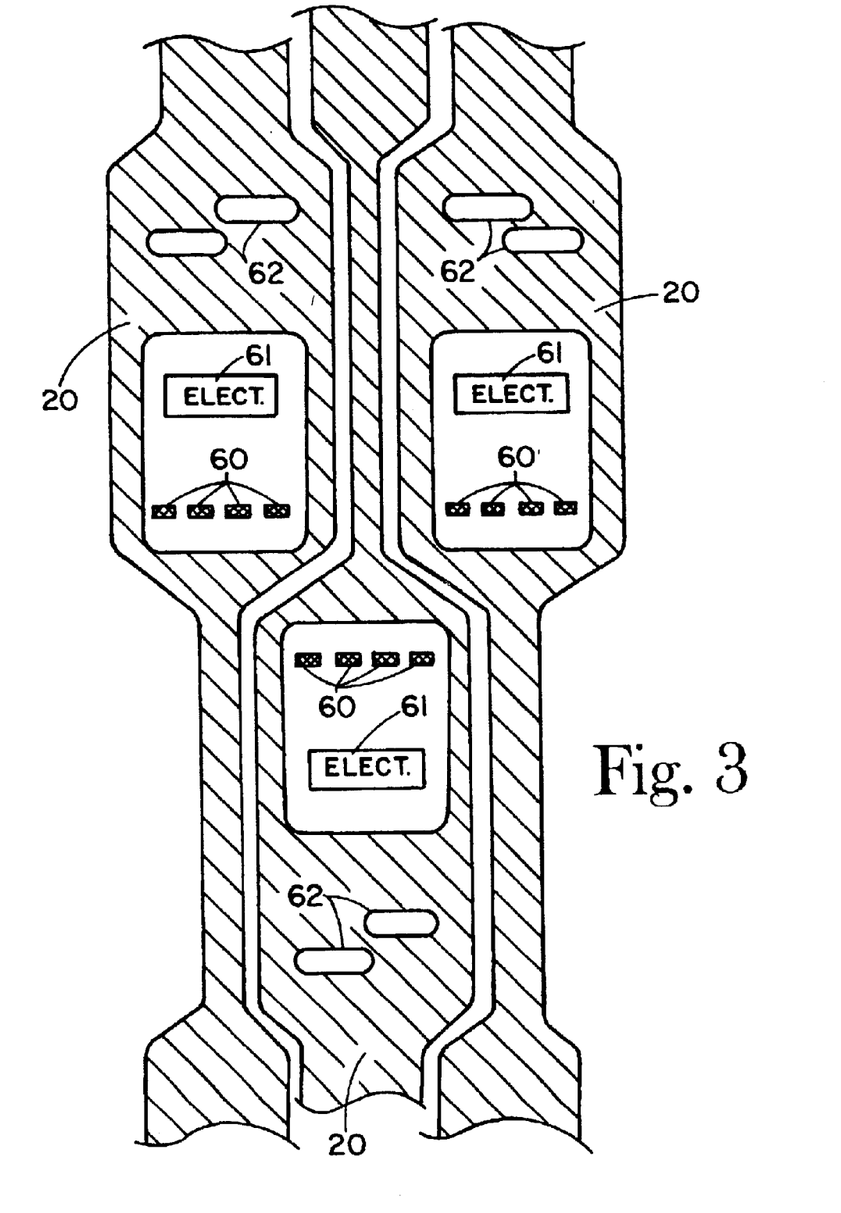
FIG. 3 is a frontal view illustrating details of the tool sensor pads.

FIG. 3 illustrates a front view of three sensor pads 20. Four Hall effect sensors 60 are shown disposed on each pad 20. Sensors 60 on each pad are disposed on a horizontal row. Other sensor disposition arrangements (not shown) can be used, such as displacing one or more sensors 60 axially (vertically as shown in FIG. 3) along a pad 20. As an example, alternating sensors could be aligned as two horizontal rows. As another example, the sensors could be "staggered" wherein each sensor 60 is disposed at a unique axial spacing along a pad 20. The sensitivity range of each sensor preferably yields a radial resolution of an arc of about 0.5 inches (in.). Stated another way, a sensor 60 responds to changes in metal content occurring within an arc of adjacent tubular, and the arc extends about 0.25 in. to either side of the center of the sensor. Other sensors with different sensitivity ranges, and thus different radial resolutions, can be used. For all sensor disposition options, radial spacings between the sensors 60 are selected so that the radial resolutions of adjacent sensors overlap. Typically, center lines of sensors are radially spaced at about 0.3 to 0.5 in. Each pad 20 also contains an electronics package 61 that distributes power and preprocesses signals detected by each of the Hall effect sensors 60. The sensors 60 and electronics 61 are hydraulically sealed from the borehole environment.

Again referring to FIG. 3, each pad 20 also contains two or more shallow reading sensors 62, whose responses are used to identify metal loss on the inner surface of the tubular. As discussed previously, the shallow reading sensors can be either reluctance type or eddy current type. Two coils of the shallow reading sensors 62 are shown disposed radially and axially along the pad 20. Alternately, the shallow reading sensors 62 could be disposed radially in a horizontal row. The shallow reading sensors 62 are also powered and controlled by the corresponding pad electronics package 61.

Still referring to FIG. 3, three pads illustrate the axial offset positioning of the entire pad array. Alternating pads are aligned along two horizontal rows. This arrangement is used so that radial spacing between the nearest Hall effect sensors on adjacent pads 20 will not exceed the radial spacing of adjacent sensors on a given pad when the pad assembly is expanded to urge the pads against the inner wall of the tubular 12. This, in turn, assures that radial resolution of all adjacent sensors overlap, and that a flaw in a tubular will not go undetected by being passed over by a "gap" in the pad array. Stated another way, complete circumferentially sensor coverage is provided around the inner tubular wall when the pad assembly is expanded. Shallow reading sensors 62 are also disposed on the pads 20 so that their radial resolutions overlap when the pad assembly is expanded. It should be understood that other axial pad offset arrangements can be used. As an example, adjacent groups of three pads can be aligned in three differing horizontal rows. As another example, each pad 20 can be aligned at a unique axial position. Both alternate examples could extend the length of the tool 11. The dimensions and disposition of the pads 20, the radial and axial dispositions of the Hall effect sensors 60, the number of Hall effect sensors, the number of pads, and the disposition and number of shallow reading sensors 62 are determined by (1) the inside diameter of the tubular being inspected and (2) by the radial distance that the expansion arms 22 can extend each pad. As an example, a pad array used to inspect 4.50 inch, 9.5 pound per foot casing may contain a different number of pads 20 with different outer surface curvature, and a different number of sensors 60, and different number of shallow reading sensors 62 than an array used to inspect 10 inch, 17 pound per foot casing.

Referring to both FIG. 2 and FIG. 3, it is desirable to "depth shift" the responses of each Hall effect sensor and each shallow reading sensor 62 to a depth reference point on the tool 11. Recall that the responses of each Hall effect sensor 60 and each shallow reading sensor 62 are used in combination to locate and to geometrically define a tubular flaw. In view of the previous discussion, it is apparent that all Hall effect sensors 60 and all shallow reading sensors 62 can not be disposed in a single plane perpendicular to the major axis of the tool 11. It is, therefore, advantageous to axially shift responses of all sensors 60 and sensors 62, prior to data processing, to a specified axial depth "reference point" on the tool 11. The reference point can be the midpoint of the pad array. Alternately, other reference points can be used such as the cable head 16 or the bull plug 37. Detected flaws can then be located precisely along the tubular 12 using depth of the tool 11 within the tubular (obtained from the depth measuring device 57 cooperating with the surface equipment 52) combined with the known tool depth reference point.

Figure 4:
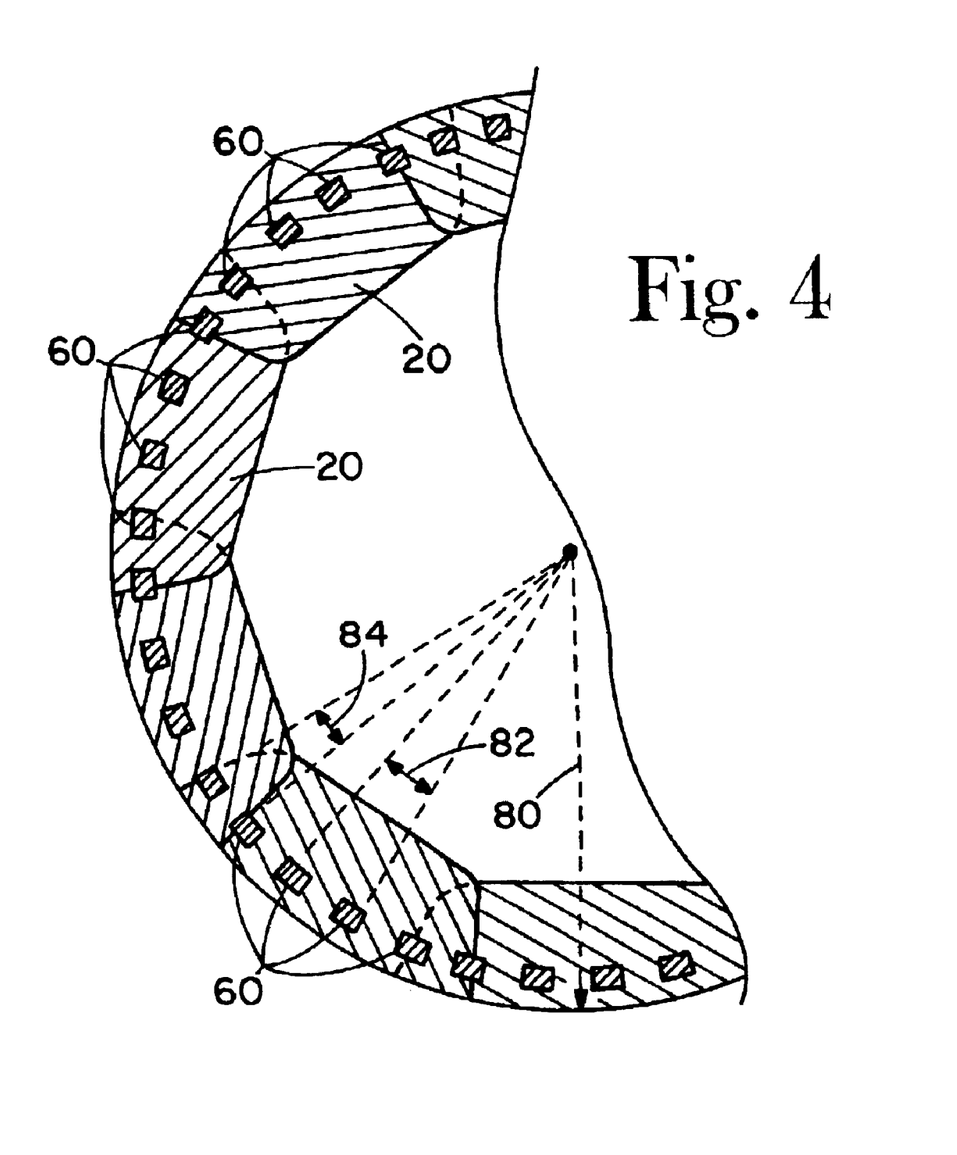
FIG. 4 is a partial cross sectional view of several sensor pads in a pad array.

FIG. 4 is partial sectional view of the pad array of the tool 11. Hall effect sensors 60 on a given pad 20 are shown as shaded or hatched to differentiate sensors on different pads 20. The extended pad array has a radius 80. The angle 82 between each Hall effect sensor 60 on a given pad 20 is such that radial spacing between sensor centers is about 0.4 inch yielding the desired overlapping of radial sensor resolution which is about 0.5 in. The sensors 60 are preferably disposed within the pad 20 and along an arc that is essentially the same as the arc defining the outer circumference of the pad 20. The sensors 60 are, thefore, isolated or shielded from the environs within the tubular. In the preferred embodiment, the outer circumference of the pad is selected to closely match the curvature of the inner surface of the tubular being inspected. This methodology assures that each sensor 60 is an equal distance from the outer surface of the pad 20, and thus an equal distance from the inner surface of the tubular. Each sensor 60 has, therefore, essentially the same radial depth of investigation into the tubular. Sensors can be displaced along arcs of multiple radii, but sensor depth of investigation corrections would be required. As discussed previously, the pad array is sized so that the angle 84 formed by the closest sensors 60 on adjacent pads is no greater than the angle 82. Radial resolution of all adjacent sensors in the pad array overlap. This assures essentially equal spacing of sensors 60 around the circumference of the pad array thereby minimizing the possibility that flaws will go undetected by passing through gaps in the extended pad assembly. The geometry of a pad array is designed to meet these radial sensor resolution and pad curvature criteria for a tubular of a given radius 80. It is necessary, therefore, to interchange pad arrays to accommodate a tubular with a substantially different radius 80.

2. Tool Operational Characteristics

Hall effect sensors operate over a wide range of temperatures. This minimizes the need for temperature compensation circuitry in the electronics packages 61 or 40. Output of a Hall effect sensor is essentially linear with respect to change in magnetic field (thus change in metal content) thereby yielding meaningful tool response over a wide range of tubular flaw conditions and simplifying interpretation techniques. The signal amplitude response of the Hall effect sensors is independent of the speed at which the logging tool 11 is conveyed along the borehole 9. Flaw measurements can be made with the tool 11 stationary, or moving at varying speeds along the borehole. From an economic viewpoint, Hall effect sensors are relatively inexpensive and require minimal maintenance.

As mentioned previously, the electronics packages 61 and 40 distribute power, and obtain the measurements from the Hall effect sensors 60. As an example, the electronics packages 61 can contain circuitry to measure and to multiplex the output signals from individual sensors and transmit these outputs to the electronics package 40 for further downhole processing using a processor contained therein. If a multiconductor logging cable 18 is used, output from sensors 60 and 62 can be telemetered to the surface for additional processing. A downhole telemetry link is preferably contained within the electronics package 40, and the uphole telemetry link is preferably contained in the surface electronics 52 (see FIGS. 1–3). If a single conductor cable is used, it is desirable to optionally preprocess and to store sensor response data in memory within the tool for subsequent downloading and processing at the surface due to telemetry bandwidth limitations. Both a processor and a memory for these operations are preferably disposed within the electronics section 40. In principle, the tool can be run on a "slick line". This mode of operation would require a downhole power supply to operate the various electronic components, and again a memory to store sensor response for subsequent processing at the surface. The tool can also be run on coiled tubing.

3. Tool Response

Figure 5:
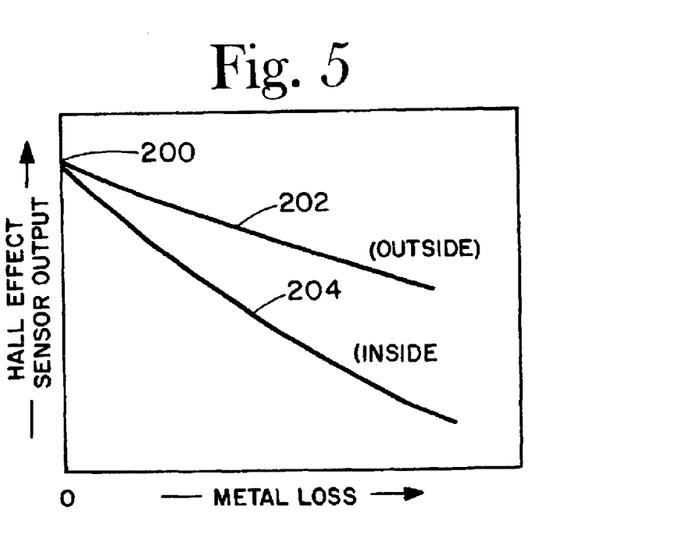
FIG. 5 is a plot of Hall effect sensor output as a function of tubular metal loss for loss at the inner tubular wall and at the outer tubular wall.

As mentioned previously, a Hall effect sensor output is approximately proportional to the magnetic field to which it is exposed. With the tubular surrounding the sensor saturated, any loss of tubular material will result in a corresponding increase in sensor output. For a flaw with a given amount of metal loss, the physical location of the flaw affects sensor response. This effect is shown conceptually in FIG. 5, which is a plot of Hall effect sensor output (ordinate) as a function of tubular metal loss (abscissa).). For this and subsequent Figures, the output of the Hall effect sensor has been inverted so as to indicate that a "loss" of material represents a "dip" on the output. In reality, loss of material will result in a corresponding increase in sensor output. Sensor output is represented by the value 200 for no metal loss. Curve 204 represents output as a function of metal loss on the inner surface of the tubular. Curve 202 represents the corresponding metal loss on the outer surface of the tubular. Hall effect sensor response is significantly less sensitive to metal loss on the outer surface of the tubular. Once the surface of metal loss is determined with shallow reading sensor measurement, Hall effect sensor responses can optionally be normalized for a given tubular size using a calibration procedure discussed in a subsequent section of this disclosure. Using the pad geometry and sensor distribution discussed previously, metal loss as little as 10 percent can be detected on the inner surface of the tubular, and approximately 20 percent on the outer surface of the tubular. FIG. 5 provides a graphical means for transforming output of a Hall effect sensor into metal loss. It should be understood that transformation of sensor output to metal loss can be obtained using alternate apparatus and methods. As an example, the illustrated transformation can be expressed mathematically and the transformation can be performed mathematically using a processor. As another example, the transformation can be expressed as a look-up table and metal loss can be obtained for a given sensor response input. As yet another example, an artificial intelligence system can be "trained" to perform the subject transform.

Figure 6:
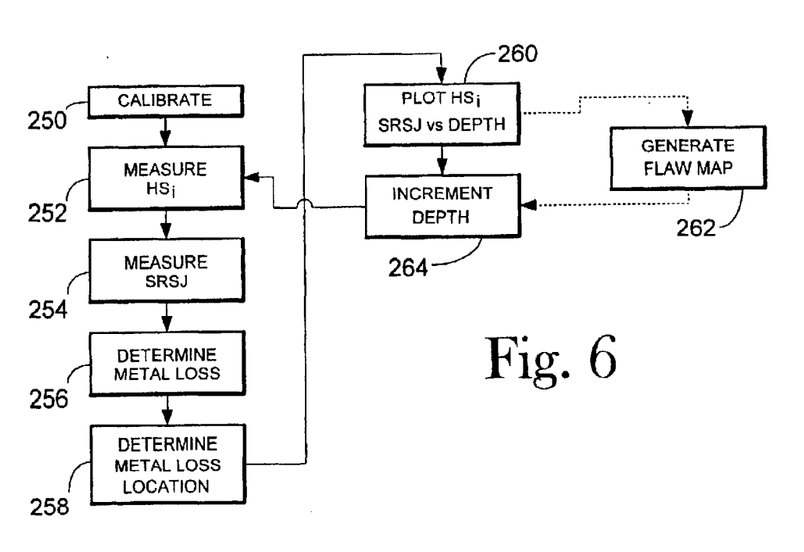
FIG. 6 illustrates conceptually data processing methods used to convert basic sensor response into a "log" of tubular flaws versus depth.
Figure 8:
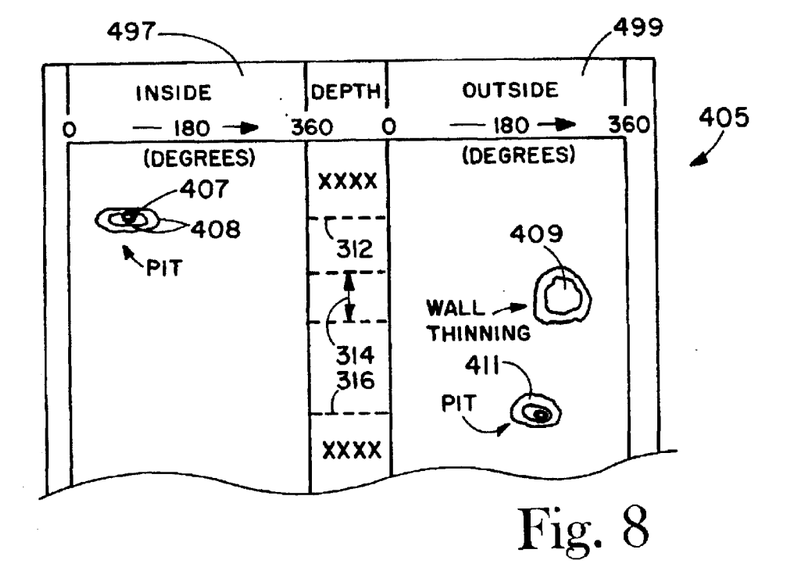
FIG. 8 illustrates a map illustrating flaws in the circumference of a tubular, as a function of depth within the tubular.

FIG. 6 illustrates conceptually data processing steps used to combine basic sensor responses into a "log" of tubular flaws. The log defines (1) the axial and optionally the radial location, and (2) illustrates the type or geometry of a flaw. For purposes of this disclosure, (1) the term "location" of the flaw will include the axial position along the length of the tubular and optionally the radial position around the circumference of the tubular. The term "geometry" of a flaw will include the shape and depth of the flaw and whether the flaw is on the inner or outer surface of the tubular. The system is calibrated at step 250. The pad assembly and distribution of sensors 60 (see FIG. 3) is selected according to the dimensions of the tubular 12 being measured. A predetermined normalization factor for that size of tubular can optionally be used to normalize outputs of the sensors 60 as a function of metal loss, once the physical position of the loss (inside or outside tubular surface) has been determined using responses of the shallow reading sensors 62. Hall effect sensor 60 outputs $HS_i$ (i=1, ..., n) are measured at step 252 for preferably all "n" sensors in the pad array. Shallow reading sensor 62 outputs $SRS_j$ (j=1, ..., m) are measured at step 254 for preferably all "m" shallow reading sensors in the pad array. Any metal loss is determined from $HS_i$ at step 256. More specifically, sensor responses are depth shifted to the tool reference point and combined with output from the depth measuring device 57. The location of any inner surface metal loss is determined from $SRS_j$ at step 258. If $HS_i$ shows a metal loss with no indication in the corresponding $SRS_j$ responses, the flaw is on the outer surface of the tubular and the amount of metal loss is then determined from $HS_i$ using the predetermined relation of the type shown as curve 202 in FIG. 5. If $HS_i$ shows a metal loss with an indication in the corresponding $SRS_j$ responses, the flaw is on the inner surface of the tubular and the amount of metal loss is then determined from $HS_i$ using the predetermined relation of the type shown as curve 204 in FIG. 5. The terms $HS_i$ and $SRS_j$ are plotted at step 260 as a function of depth at which the measurements are made. Optionally, a map of the tubular wall can be generated as a function of depth along the tubular at step 262. The map is essentially a "flattened" view of the tubular, with the shape, location and radial depth of any detected flaws shown graphically around the circumference of the tubular. An example of a map is illustrated in FIG. 8. Depth is incremented at step 264 and steps 252 through 264 are repeated thereby generating a "log" of tubular flaws as a function of depth.

Referring to FIGS. 1, 3 and 6, data processing can be performed at optional locations within the system. As an example, multiplexing and some preprocessing of the response of sensors 60 and 62 can be performed in the pad mounted electronics packages 61. This conserves telemetry bandwidth. Additional processing can occur in a downhole processor (not shown) within the downhole electronics package 40. Raw data, or data in various stages of conditioning and processing, can be stored within a memory (not shown) in the electronics package 40 for subsequent retrieval and processing at the surface of the earth. Data, either raw or partially processed, can be telemetered to a processor (not shown) within the surface equipment 52 via the logging cable 18 for additional processing. As an example, it is preferred to generate any logs using the surface equipment 52 since tool depth is supplied to the surface equipment by the depth measuring device 57.

Figure 7:
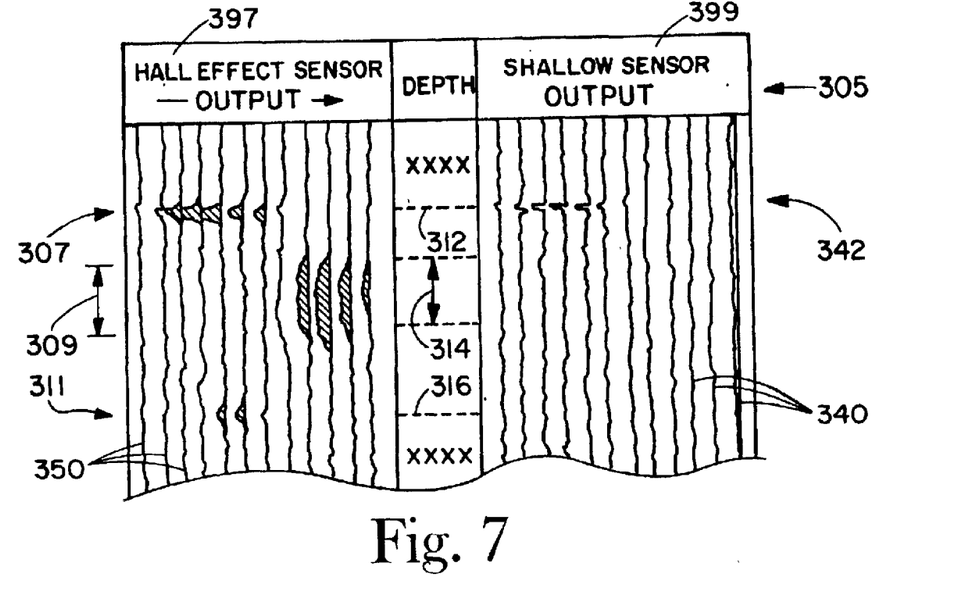
FIG. 7 illustrates a log generated by the tubular inspection system in the form of sensor responses to flaws as a function of axial and circumferencial position within the tubular.

For the subsequent discussion of FIG. 7, it is again noted that the output of the Hall effect sensors has been inverted, so as to indicate a "dip" when "loss" of material is present. The true output of the sensor increases with material loss. FIG. 7 illustrates a "log" 305 of the tubular inspection system in the form of recordings of sensor responses as a function of axial position within the tubular. Field 397 shows outputs 330 from the Hall effect sensors 60 as a function of depth along the tubular 12. Some sensor outputs are omitted for clarity. Field 399 shows corresponding measurements 340, as a function of depth, from the shallow reading sensors 62. Again, some measurements have been omitted for clarity. The full circumference of the tubular is, however, represented. All sensor responses have been depth shifted as discussed previously. Combination of sensor responses to determine position and geometry of flaws is illustrated by the following examples. An increase in Hall effect sensor outputs 307 is seen over an arc at a depth 312. Referring to the field 399 of shallow reading sensor measurements 340, corresponding responses 342 from the sensors 62 are seen at the same depth 312. This indicates that the flaw is on the inner tubular wall, and considering the relatively short axial extent and arc of the anomalies, the flaw would likely be interpreted as a pit in the inner wall. Increases in some Hall effect sensor outputs 309 are seen over a depth interval 314. There is no corresponding activity in the shallow response sensor measurements 340 in the log field 399 at this depth interval. This indicates that the flaw is in the outer tubular wall. Considering the relatively long arc and the relatively long axial extent of the of the Hall effect sensor anomalies 309, the flaw would likely be interpreted as a corrosion area on the outer tubular wall. Increases in some Hall effect sensor outputs 311 are seen at a depth 316. Again there is no corresponding activity in the shallow response sensor measurements 340 at depth 316 in the field 399. This indicates that the flaw is in the outer tubular wall. Considering the relatively short arc and the relatively short axial extent of the of the Hall effect sensor anomalies, the flaw would again be interpreted as a pit on the outer tubular wall.

The above illustrates logic used in combining responses of Hall effect sensors and shallow reading sensors to obtain location and geometry of tubular flaws. This combination can be performed by human inspection of the log fields 397 and 399 illustrated in FIG. 7. Alternately, mathematical relationships can be developed to "compute" flaw location and geometry. Furthermore, artificial intelligence systems can be "trained" to combine Hall effect sensor and shallow reading sensor output to generate the desired flaw location and geometry data.

FIG. 8 illustrates a map 405 of the circumference of a tubular, as a function of depth along the tubular. The map is generated from data illustrated in FIG. 7, and illustrates graphically the geometry (shape and radial depth) and axial and radial position of the detected flaws. Field 497 represents the inner wall of the tubular with circumference extending from 0 to 360 degrees. Field 499 represents the outer wall of the tubular with circumference extending again from 0 to 360 degrees. Degrees can be relative to tool orientation, or can be absolute if an azimuthal direction device is run in conjunction with the tubular inspection tool. Hall effect sensor and corresponding shallow response sensor measurements are combined with initial calibration data, defining the unperturbed dimensions of the tubular, to generate the maps. Attention is drawn to the inside wall field 497, which illustrates a "map" 407 of the pit 307 (at depth 312) which was discussed previously in FIG. 7. It is known that the pit is on the inside wall since corresponding shallow response sensor activity 342 is observed at depth 312. Contour lines 408 show the radial depth of the map 407 of the pit. Radial depth information is obtained by combining the magnitudes of excursions of the Hall effect sensor curves 307 with the predetermined relationship 204 relating sensor output magnitude as a function of metal loss (see FIG. 5), and with the tool calibration for a particular size tubular being inspected. Flaw shape is obtained from the number of adjacent excursions and the axial extent of the excursions in Hall effect sensor responses. Attention is next drawn to the outside wall field 499 which illustrates a "map" 409 of the corrosion 342 over the depth interval 314 and also discussed previously with FIG. 7. It is known that the corrosion is on the outside wall since no corresponding shallow response sensor activity 340 is observed over the depth interval 314. Contour lines again show the radial depth and outline the shape (as discussed above) of the corrosion flaw 409. Finally, attention is next drawn to the outside wall field 499 which illustrates a "map" 411 of the pit 311 at depth 316 discussed previously with FIG. 7. Again, it is known that the corrosion is on the outside wall since no corresponding shallow response sensor activity 340 is observed at depth 316. Contour lines again show the shape and radial depth (as discussed above) of the pit 411. It should be understood that radial depth and shape (i.e. flaw "geometry") can be indicated by alternate means such as shading, color coding and the like. It should also be understood that a three dimensional, rotateable image of the tubular with flaws can be generated from previously discussed measured and calibration data.

One skilled in the art will appreciate that the present invention can be practiced by other than the described embodiments, which are presented for purposes of illustration and not limitation, and the present invention is limited only by the claims that follow.

What is claimed is:

1. In a well borehole, a system for measuring a flaw in a ferromagnetic tubular within said borehole, the system comprising:
   (a) a tool conveyable within said tubular;
   (b) a pad array disposed in said tool and comprising a plurality of pads;
   (c) means for urging each of said plurality of pads against an inner wall of said tubular;
   (d) a plurality of Hall effect sensors disposed in each of said pads, wherein each said pad comprises at least two said Hall effect sensors positioned, within each said pad, in a plane perpendicular to the major axis of said tool and at equal radial spacing and at equal distance from an outer surface of said pad;
   (e) circuitry for measuring responses of said Hall effect sensors to a saturated magnetic field induced within said tubular; and
   (f) located within said tool, a permanent magnet assembly comprising a core and two permanent magnetic poles disposed at opposing ends of said core thereby inducing said magnetic field within said tubular.

2. The system of claim 1 further comprising a processor for transforming said responses of said Hall effect sensors to determine an amount of ferromagnetic material loss in said flaw.

3. The system of claim 2 further comprising a logging cable with a first end operationally connected to said tool and a second end operationally connected to surface equipment located at the surface of the earth.

4. The system of claim 3 further comprising:
(a) at least one shallow reading sensor disposed within each said pad; and
(b) a processor for combining said responses from said Hall effect sensors and responses from said shallow reading sensors to determine position and geometry of said flaw.

5. In a well borehole, a system for measuring a flaw in a ferromagnetic tubular within said borehole, the system comprising:
(a) a tool conveyable within said tubular;
(b) a pad array disposed in said tool and comprising a plurality of pads;
(c) means for urging each of said plurality of pads against an inner wall of said tubular;
(d) a plurality of Hall effect sensors disposed in each of said pads;
(e) circuitry for measuring responses of said Hall effect sensors to a saturated magnetic field induced within said tubular;
(f) located within said tool, a permanent magnet assembly comprising a core and two permanent magnetic poles disposed at opposing ends of said core thereby inducing said magnetic field within said tubular;
(g) a processor for transforming said responses of said Hall effect sensors to determine an amount of ferromagnetic material loss in said flaw;
(h) a logging cable with a first end operationally connected to said tool and a second end operationally connected to surface equipment located at the surface of the earth; and;
(i) at least one shallow reading sensor disposed within each said pad wherein said responses from said Hall effect sensors and responses from said shallow reading sensors are combined in said processor to determine position and geometry of said flaw; wherein
(j) four said Hall effect sensors are disposed, within each said pad, in a plane perpendicular to the major axis of said tool and at equal radial spacing and at equal distance from an outer surface of said pad.

6. The system of claim 5 wherein amplitudes of said responses of said Hall effect sensors are independent of relative motion between said Hall effect sensor and said flaw.

7. The system of claim 5 further comprising a depth measuring device which cooperates with said logging cable and said processor to define the axial location of said tool within said well borehole.

8. The system of claim 5 wherein each said pad comprises two said shallow reading sensors disposed on said outer surface of each said pad and displaced radially and axially from each other.

9. The system of claim 8 wherein said responses from said Hall effect sensors and said responses from said shallow reading sensors are depth shifted to a tool reference point.

10. The system of claim 9 wherein said axial location of said tool within said well borehole an said reference point are combined to determine an axial location of said flaw along said tubular.

11. The system of claim 8 wherein said shallow reading sensors are disposed within each of said pads so that radial resolution of each said shallow reading sensor overlaps radial resolution of adjacent shallow reading sensors when said plurality of pads are urged against said inner wall of said tubular.

12. The system of claim 5 wherein said Hall effect sensors are disposed within each of said pads so that radial resolution of each said Hall effect sensor overlaps radial resolutions of adjacent Hall effect sensors when said plurality of pads are urged against said inner Wall of said tubular.

13. The system of claim 5 wherein said shallow reading sensors are responsive to eddy currents within said tubular.

14. The system of claim 5 wherein said shallow reading sensors are responsive to reluctance within said tubular.

15. In a well borehole, a method for measuring a flaw in a ferromagnetic tubular within said borehole, the method comprising:
(a) conveying a tool within said tubular;
(b) providing a pad array disposed in said tool and comprising a plurality of pads;
(c) urging each of said plurality of pads against an inner wall of said tubular;
(d) disposing four Hall effect sensor in each of said pads;
(e) measuring responses of said Hall effect sensors to a saturated magnetic field induced within said tubular; and
(f) inducing said magnetic field within said tubular with a permanent magnet assembly disposed within said tool and comprises a core and two permanent magnetic poles disposed at opposing ends of said core; wherein
(g) said four Hall effect sensors in each said pad are disposed in a plane perpendicular to the major axis of said tool and at equal radial spacing and at equal distance from an outer surface of said each pad.

16. The method of claim 15 further comprising transforming said responses of said Hall effect sensors to determine an amount of ferromagnetic material loss in said flaw.

17. The method of claim 16 further comprising conveying said tool within said tubular with a logging cable with a first end of said cable operationally connected to said tool and a second end of said cable operationally connected to surface equipment located at the surface of the earth.

18. The method of claim 17 further comprising:
(a) disposing at least one shallow reading sensor within each said pad; and
(b) combining said responses from said Hall effect sensors and responses of said shallow reading sensors to determine position and geometry of said flaw.

19. The method of claim 18 wherein said at least one shallow reading sensor is responsive to reluctance within said tubular.

20. In a well borehole, a method for measuring a flaw in a ferromagnetic tubular within said borehole, the method comprising:
(a) conveying a tool within said tubular
(b) providing a pad array disposed in said tool and comprising a plurality of pads;
(c) urging each of said plurality of pads against an inner wall of said tubular;
(d) disposing a plurality of Hall effect sensors in each of said pads;
(e) measuring responses of said Hall effect sensors to a saturated magnetic field induced within said tubular;
(f) inducing said magnetic field within said tubular with a permanent magnet assembly disposed within said tool and comprises a core and two permanent magnetic poles disposed at opposing ends of said core;
(g) forming said responses of said Hall effect sensors to determine an amount of ferromagnetic material loss in said flaw;

(h) conveying said tool within said tubular with a logging cable with a first end of said cable operationally connected to said tool and a second end of said cable operationally connected to surface equipment located at the surface of the earth;

(i) disposing at least one shallow reading sensor within each said pad; and (j) combining said responses from said Hall effect sensors and responses of said shallow reading sensors to determine position and geometry of said flaw; wherein (k) for said Hall effect sensors are disposed within each pad and in a plane perpendicular to the major axis of said tool and at equal radial spacing and at equal distance from an outer surface of said each pad.

21. The method of claim 20 wherein amplitudes of said responses of said Hall effect sensors are independent of relative motion between said Hall effect sensor and said flaw.

22. The method of claim 20 further comprising determining the axial location of said tool within said tubular with a depth measuring device that cooperates with said logging cable.

23. The method of claim 20 comprising disposing two said shallow reading sensors on said outer surface of each pad and displacing said shallow reading sensors radially and axially from each other.

24. The method of claim 23 comprising depth shifting said responses from said Hall effect sensors and said responses from said shallow reading sensors to a tool reference point.

25. The method of 24 comprising combining said axial location of said tool within said tubular and said reference point to define an axial location of said flaw along said tubular.

26. The method of claim 23 comprising positioning each said shallow reading sensor within each of said pads so that radial resolution of each shallow reading sensor overlaps radial resolution of adjacent shallow reading sensors when said plurality of pads are urged against said inner wall of said tubular.

27. The method of claim 20 comprising positioning each of said Hail effect sensors within each of said pads so that radial resolution of each said Hall effect sensor overlaps radial resolutions of adjacent Hall effect sensors when said plurality of pads are urged against said inner wall of said tubular.

28. The method of claim 20 wherein said at least one shallow reading sensor is responsive to eddy currents within said tubular.

* * * * *